(12) United States Patent
Helton et al.

(10) Patent No.: US 6,936,601 B2
(45) Date of Patent: *Aug. 30, 2005

(54) COMPOSITIONS FOR TREATING PAIN

(75) Inventors: David Reed Helton, Irvine, CA (US); Harlan E. Shannon, Carmel, IN (US); Daniel E. Womer, Thornton, CO (US); Mary Jeanne Kallman, Greenfield, IN (US)

(73) Assignee: Eli Lilly and Company, Indianapolis, IN (US)

( * ) Notice: Subject to any disclaimer, the term of this patent is extended or adjusted under 35 U.S.C. 154(b) by 193 days.

This patent is subject to a terminal disclaimer.

(21) Appl. No.: 10/224,224

(22) Filed: Aug. 15, 2002

(65) Prior Publication Data

US 2003/0013689 A1 Jan. 16, 2003

Related U.S. Application Data

(62) Division of application No. 09/498,047, filed on Feb. 4, 2000, now Pat. No. 6,444,665, which is a continuation of application No. 08/823,458, filed on Mar. 24, 1997, now abandoned.

(60) Provisional application No. 60/014,152, filed on Mar. 25, 1996.

(51) Int. Cl.$^7$ ............................................. A61K 31/554
(52) U.S. Cl. ................................................ 514/211.13
(58) Field of Search ........................... 514/211.13, 649

(56) References Cited

U.S. PATENT DOCUMENTS

| | | | |
|---|---|---|---|
| 3,704,245 A | 11/1972 | Umio et al. ................. 260/327 |
| 4,879,288 A | 11/1989 | Warawa et al. ............. 514/211 |
| 5,045,539 A | 9/1991 | Helsley et al. ............. 514/212 |
| 5,112,838 A | 5/1992 | Perregaard et al. ......... 514/323 |
| 5,229,382 A | 7/1993 | Chakrabarti et al. ........ 514/220 |
| 5,238,945 A | 8/1993 | Perregaard et al. ......... 514/323 |
| 5,246,935 A | 9/1993 | Jeppesen et al. ............ 514/253 |
| 5,605,897 A | 2/1997 | Beasley, Jr. et al. ........ 514/220 |
| 5,945,416 A * | 8/1999 | Shannon et al. ............ 514/220 |
| 6,444,665 B1 * | 9/2002 | Helton et al. ............... 514/220 |

FOREIGN PATENT DOCUMENTS

ZA           930694          2/1993

OTHER PUBLICATIONS

Dahlin et al., "The Merck Index, an encyclopedia of chemicals, drugs and biologicals" published 1983 by Merck & Co., Inc. (N.J.), see pate 7, abstract No. 39.

Meltzer et al., Derwent Drug File Abstracts, Abstract No. 94036074, (1994).

Barkin et al., Derwent Drug File Abstracts, Abstract No. 94–43595, (1994).

Double–blind Trial of Fluoxetine: Chronic daily headache and migraine, Saper, JR et al., Michigan Head Pain and Neurological Institute, Apr. 1995, 35(4):233.

Double–blind Trial of Fluoxetine: Chronic daily headache and migraine, Saper, JR et al., Michigan Head Pain and Neurological Institute, Oct. 1994, 34(9) pp. 497–502.

Br. J. Pharmacol. (England), Jul. 1994, 112(3) pp. 741–744, Laboratory of Molecular and Cellular Neurobiology, National Institute on Alcohol Abuse and Alcoholism, Rockville, MD 20852, Effects of antidepressants on the inward current mediated by 5–HT3 receptors in rat nodose ganglion neurons.

* cited by examiner

*Primary Examiner*—Phyllis G. Spivack
(74) *Attorney, Agent, or Firm*—Nelson L. Lentz

(57) ABSTRACT

The present invention provides compositions for treating pain using an atypical antipsychotic compound that is seroquel in combination with another Drug Used in the Treatment of Pain.

10 Claims, No Drawings

COMPOSITIONS FOR TREATING PAIN

This is a divisional application of Ser. No. 09/498,047, filed Feb. 4, 2000, U.S. Pat. No. 6,444,665 which is a continuation application of Ser. No. 08/823,458, filed Mar. 24, 1997, abandoned, which claims priority to U.S. Provisional Application No. 60/014,152, filed Mar. 25, 1996.

FIELD OF THE INVENTION

This invention provides a method for using an atypical antipsychotic compound selected from the group consisting of risperidone, clozapine, seroquel, sertindole, ziprasidone, and zotepine for the treatment of pain.

BACKGROUND OF THE INVENTION

This invention relates to the treatment of pain using atypical antipsychotic compounds to provide analgesic activity.

Surprisingly, we have discovered that atypical antipsychotic compounds can be particular useful for treating pain. The analgesic effect may be further enhanced when used in combination with one or more another Drug Used in the Treatment of Pain compounds. More specifically, the invention provides a method of treating pain in humans using an atypical antipsychotic compound.

There are drugs used in the treatment of pain which known in the literature and to the skilled artisan. see for example, Merck Manual, 16th Ed. (1992) p. 1409.

More active analgesics are in constant demand because they offer the attractive possibility of relieving pain with reduced dosages, thereby diminishing the expected side effects and toxicity that would otherwise result from higher dosages. It would be particularly desirable to acquire a synergistic combination effect to further reduce dosages and diminish side effects. Such a composition is a subject of the present invention.

Certain compounds have been disclosed as being atypical antipsychotics which can be useful for treating schizophrenia or related psychotic conditions. Applicants have discovered that atypical antipsychotic compounds selected from the group consisting of risperidone, clozapine, seroquel, sertindole, ziprasidone, and zotepine can be useful for the treatment of pain and may provide a synergistic effect when administered with one or more other drugs used in the treatment of pain.

SUMMARY OF THE INVENTION

The present invention provides a method for treating pain, comprising administering an effective amount of an atypical antipsychotic selected from the group consisting of risperidone, clozapine, seroquel, sertindole, ziprasidone, and zotepine to a patient in need thereof.

The present invention further provides a method for treating pain comprising administering to a patient in need thereof, an analgesic composition comprising an atypical antipsychotic or a pharmaceutically acceptable salt thereof; and another Drug Used in the Treatment of Pain, in a weight ratio of one part atypical antipsychotic to from about one part to about one thousand (1,000) parts of another Drug Used in the Treatment of Pain.

A preferred composition is a weight ratio of atypical antipsychotic to another Drug Used in the Treatment of Pain of from about 1 part atypical antipsychotic to from about 1 part to about 100 parts of another Drug Used in the Treatment of Pain. An especially preferred ratio is from about 1 part atypical antipsychotic to from about 1 to about 30 parts another Drug Used in the Treatment of Pain. A further preferred ratio may be from about 1 part atypical antipsychotic to from about 1 part to about 10 parts another Drug Used in the Treatment of Pain. A final preferred ratio may be from about 1 part atypical antipsychotic to from about 1 to about 3 parts another Drug Used in the Treatment of Pain.

Preferably another Drug Used in the Treatment of Pain is one or more compounds selected from the group consisting of aspirin, acetominophen, paracetamol, indomethacin, Tylenol #3, tricyclic antidepressants (for example desipramine, imipramine, amytriptiline, nortriptile), anticonvulsants (for example, carbamazepine, valproate), and serotonin reuptake inhibitors (for example, fluoxetine, paraoxetine, sertraline), mixed serotonin-norepinephrine reuptake inhibitors (for example venlafaxine, duloxetine), serotonin receptor agonists and antagonists, cholinergic (muscarinic and nicotinic) analgesics, adrenergic agents, and neurokinin antagonists.

Particularly preferred Drug Used in the Treatment of Pain are selected from the group consisting of aspirin, acetominophen, ketorolac, allopurinol, methysergide maleate, and methotrimeprazine.

The invention further provides a composition for treating pain comprising an atypical antipsychotic or a pharmaceutically acceptable salt or solvate thereof and one or more another Drug Used in the Treatment of Pain in a weight ratio of atypical antipsychotic to another Drug Used in the Treatment of Pain of from about one (1) part atypical antipsychotic to from about 1 part to about 1000 parts Drug Used in the Treatment of Pain.

DETAILED DESCRIPTION OF THE INVENTION

Another Drug Used in the Treatment of Pain used primarily for the symptomatic relief of pain may be divided into four major groups: 1) opiate analgesics; 2) nonopiate analgesics; 3) analgesics and antipyretics; and 4) nonsteroidal antiinflammatory drugs. Other compounds contemplated herein as "Drug Used in the Treatment of Pain" include, but are in no way limited to other drug classes which might be used with atypical antipsychotics for the treatment of pain to provide a synergistic effect, for example, acetominophen, paracetamol, indomethacin, Tylenol #3, tricyclic antidepressants (for example desipramine, imipramine, amytriptiline, nortriptile), anticonvulsants (for example, carbamazepine, valproate), and serotonin reuptake inhibitors (for example, fluoxetine, paraoxetine, sertraline), mixed serotonin-norepinephrine reuptake inhibitors (for example venlafaxine, duloxetine), serotonin receptor agonists and antagonists, cholinergic (muscarinic and nicotinic) analgesics, adrenergic agents, and neurokinin antagonists. Some preferred another Drug Used in the Treatment of Pain s are selected from acetominphen, cholinergic analgesics, and neurokinin anatagonists. Other preferred Drug Used in the Treatment of Pain include tricyclic antidepressants, anticonvulsants, and serotonin reuptake inhibitors.

Another preferred group of Drug Used in the Treatment of Pain is nonopiate analgesics. The term "nonopiate analgesics" refer to compounds including, but not limited to Butorphanol, Propoxyphene, meperidine, alphaprodine hydrochloride, fentanyl, and tramadol.

Another preferred group of Drug Used in the Treatment of Pain is "analgesics and antipyretics" wherein the term refers to compounds such as, but not limited to, acetominophen, ketorolac, allopurinol, methysergide maleate, and methotrimeprazine.

Applicants appreciate that a new Drug Used in the Treatment of Pain may be in development, and the present invention contemplates a synergistic composition comprising such new agents with atypical antipsychotic as well.

As used herein the term "atypical antipsychotic" shall refer to a compound selected from the group consisting of risperidone, clozapine, seroquel, sertindole, ziprasidone, and zotepine.

Risperidone is a known antipsychotic compound currently marketed by Janssen and claimed by U.S. Pat. No. 5,246,935 which is hereby incorporated by reference in its entirety.

Clozapine is a well known atypical antipsychotic compound currently marketed by Sandoz.

Seroquel is a known compound claimed by U.S. Pat. No. 4,879,288 which is hereby incorporated by reference in its entirety.

Sertindole is a known compound and is claimed by U.S. Pat. Nos. 5,112,838 and 5,2238,945 each of which is hereby incorporated by reference in their entirety.

Ziprasidone is a known compound and is claimed in EP281309-A which is readily available to the skilled artisan. Ziprasidone has the following structure:

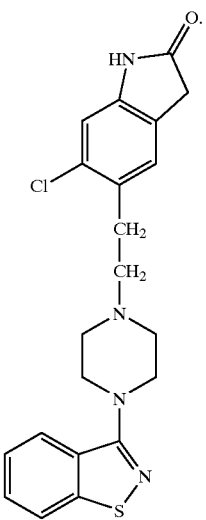

Zotepine is a known compound claimed in U.S. Pat. No. 3,704,245 which is hereby incorporated by reference in its entirety. Zotepine has the following structure:

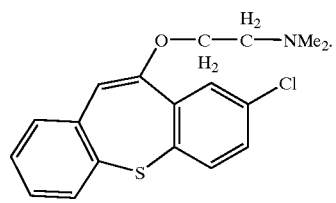

As used herein, the term "mammal" shall refer to the Mammalia class of higher vertebrates. The term "mammal" includes, but is not limited to, a human. The term "treating" as used herein includes prophylaxis of the named condition or amelioration or elimination of the condition once it has been established.

As used herein the term "Drug Used in the Treatment of Pain" refers to compounds known to be clinically useful as analgesics. The term refers to one or more such compounds. Thus, the term Drug Used in the Treatment of Pain can refer to one known analgesic or a combination comprising from two to three known analgesic compounds. Drug Used in the Treatment of Pain are most preferably selected from the compounds named herein.

In the composition of this invention an atypical antipsychotic or a pharmaceutically acceptable salt thereof and one or more Drug Used in the Treatment of Pain are combined in a weight ratio of atypical antipsychotic to Drug Used in the Treatment of Pain of from about one part atypical antipsychotic to from about 1 to about 1000 parts Drug Used in the Treatment of Pain.

A preferred composition is a weight ratio of atypical antipsychotic to another Drug Used in the Treatment of Pain is from about 1 part atypical antipsychotic to from about 1 part Drug Used in the Treatment of Pain to about 100 parts Drug Used in the Treatment of Pain. An especially preferred ratio is from about 1 to about 30. A further preferred ratio may be from about 1 to about 10. A final preferred ratio may be from about 1 to about 3.

Atypical antipsychotics are effective over a wide dosage range; however, it is desirable to administer a dosage that is as low as possible. The amount of Drug Used in the Treatment of Pain present in the composition is adjusted as described above in ratio to the atypical antipsychotic dosage. For example, dosages per day of the atypical antipsychotic will normally fall within the range of about 0.5 mg to about 300 mg per day and the Drug Used in the Treatment of Pain in the composition would be from 3 to 1000 times this amount.

However, it will be understood that the amount of the compound actually administered will be determined by a physician, in the light of the relevant circumstances including the condition to be treated, the choice of compound to be administered, the age, weight, and response of the individual patient, the severity of the patient's symptoms, and the chosen route of administration, and therefore the above dosage ranges are not intended to limit the scope of the invention in any way. While the present compounds are preferably administered orally to humans susceptible to or suffering from pain, the compounds may also be administered by a variety of other routes such as the transdermal, parenterally, subcutaneous, intranasal, intramuscular and intravenous routes. Such formulations may be designed to provide delayed or controlled release using formulation techniques which are known in the art.

As used herein the term "treating" includes prophylaxis of a physical and/or mental condition or amelioration or elimination of the developed physical and/or mental condition once it has been established or alleviation of the characteristic symptoms of such condition.

As used herein the term "pain" shall refer to all types of pain. Preferredly, the term shall refer to chronic pains, such as neuropathic pain, and post-operative pain, chronic lower back pain, cluster headaches, herpes neuralgia, phantom limb pain, central pain, dental pain, neuropathic pain, another Drug Used in the Treatment of Pain—resistant pain, visceral pain, surgical pain, bone injury pain, pain during labor and delivery, pain resulting from burns, including sunburn, post partum pain, migraine, angina pain, and genitourinary tract-related pain including cystitis, the term shall also preferredly refer to nociceptive pain or nociception. The dosage administered will, of course, vary depending on known factors such as the pharmacodynamic characteristics of the particular agent, and its mode and route of administration; age, health, and weight of the recipient; nature and extent of the symptoms, kind of concurrent treatment, frequency of treatment, and the effect desired. Usually, the daily dosage can be such that the active ingredient is administered at a daily dosage of from about 0.2 mg to about 50 mg atypical antipsychotic and from about 0.6 to about 500 mg of another Drug Used in the Treatment of Pains.

Compositions suitable for internal administration contain from about one half (0.5) milligrams to about 600 milligrams of active ingredient per unit. In these pharmaceutical compositions, the active ingredient will ordinarily be present in an amount of from about 0.5% to about 95% by weight based on the total weight of the composition.

Typical compositions include atypical antipsychtoic or a pharmaceutically acceptable acid addition salt thereof and one or more another Drug Used in the Treatment of Pains, associated with a pharmaceutically acceptable excipient which may be a carrier, or a diluent or be diluted by a carrier, or enclosed within a carrier which can be in the form of a capsule, sachet, paper, or other container. In making the compositions, conventional techniques for the preparation of pharmaceutical compositions may be used. For example, the active compound will usually be mixed with a carrier, or diluted by a carrier, or enclosed within a carrier which may be in the form of a ampoule, capsule, sachet, paper, or other container. When the carrier serves as a diluent, it may be solid, semi-solid, or liquid material which acts as a vehicle, excipient, or medium for the active compound. The active compound can be adsorbed on granular solid container for example in a sachet. Some examples of suitable carriers are water, salt solutions, alcohols, polyethylene glycols, polyhydroxyethoxylated castor oil, gelatine, lactose, amylose, magnesium stearate, talc, silicic acid, fatty acid monoglycerides and diglycerides, pentaerythritol fatty acid esters, hydroxymethylcellulose and polyvinylpyrrolidone. The formulations may also include wetting agents, emulsifying and suspending agents, preserving agents, sweetening agents, or flavoring agents. The formulations of the invention may be formulated so as to provide quick, sustained, or delayed release of the active ingredient after administration to the patient by employing procedures well known in the art.

The pharmaceutical preparations can be sterilized and mixed, if desired, with auxiliary agents, emulsifiers, salt for influencing osmotic pressure, buffers and/or coloring substances and the like, which do not deleteriously react with the active compounds.

For parenteral application, particularly suitable are injectable solutions or suspensions, preferably aqueous solutions with the active compound dissolved in polyhydroxylated castor oil.

Tablets, dragees, or capsules having talc and/or a carbohydrate carrier or binder or the like are particularly suitable for oral application. Preferable carriers for tablets, dragees, or capsules include lactose, corn starch, and/or potato starch. A syrup or elixir can be used in cases where a sweetened vehicle can be employed.

The compositions of this invention may be suitable for administration to an animal. Such animals include both domestic animals, for example livestock, laboratory animals, and household pets, and non-domestic animals such as wildlife. More preferredly, the animal is a vertebrate. Most preferredly, a compound of this invention shall be administered to a mammal. It is especially preferred that the animal is a domestic mammal or a human. The most preferred mammal is a human. For such purposes, a compound of this invention may be administered as a feed additive.

Utility Test Metbods

The unexpectedly enhanced analgesic activity of the composition of the invention is evidenced by tests intially conducted on mice. Mice weighing from about 18–25 grams at the time of testing are used for the following studies. All mice are dosed by the oral route with a Drug Used in the Treatment of Pain and/or an atypical antipsychotic.

Mouse Writhing Test

An accepted standard for detecting and comparing the analgesic activity of different classes of analgesic compounds for which there is a good correlation with human analgesic activity is the prevention of acetic acid induced writhing in mice. [R. Koster et al. Acetic acid for analgesic screening. Fed. Proc. 18:412, 1959].

Mice, treated with various doses of atypical antipsychotic, another Drug Used in the Treatment of Pain, an atypical antipsychotic:Drug Used in the Treatment of Pain composition, or vehicle are injected intraperitoneally with a standard challenge dose of acetic acid 5 minutes prior to a designated observation period. The acetic acid is prepared as a 0.55% solution and injected at a volume of 0.1 ml/10 grams of body weight. For scoring purposes a "writhe" is indicated by whole body stretching or contracting of the abdomen during an observation period beginning about five minutes after the administration of acetic acid.

Sciatic Nerve Ligation Model

An accepted model for assessment of neuropathic pain analgesia is the sciatic nerve ligation model [Bennett, G. J. and Xie, Y. -K. A peripheral mononeuropathy in rat that produces disorders of pain sensation like those seen in man. Pain 33 (1986) 87–107; Lee, Y. -W., Chaplan, S. R. and Yaksh, T. L.: Systemic and supraspinal, but not spinal, opiates suppress allodynia in a rat neuropathic pain model. Neuroci Lett 186 (1995) 111–114]. Rats are anesthetized and a nerve ligation procedure performed. The common sciatic nerve is exposed and 4 ligatures tied loosely around it with about 1 mm spacing. One day to 10 weeks after surgery, the nociceptive testing is performed. Responses to noxious heat are determined by placing the rats in a chamber with a clear glass floor and aiming at the plantar surface of the affected foot a radiant heat source from beneath the floor. Increased latency to withdraw the hindpaw is demonstrative of analgesic activity. Responses to normally innocuous mechanical stimuli is determined by placing the rats in a chamber with a screen floor and stimulating the plantar surface of the hind paw with graduated von Frey hairs which are calibrated by the grams of force required to bend them. Rats with sciatic nerve ligation respond to lower grams of mechanical stimulation by reflexive withdrawal of the foot than unoperated rats. This response to stimuli which are normally innocuous is termed allodynia. Increases in the grams of mechanical force required to produce foot withdrawal is demonstrative of antiallodynic activity.

Formalin Test

The formalin test is a well accepted model of inflammatory pain [Malmberg, A. B. and Yaksh, T. L.: Antinociceptive actions of spinal nonsteroidal anti-inflammatory agents on the formalin test in the rat. The Journal of Pharmacology and Experimental Therapeutics 263 (1992) 136–146]. Rats are anesthetized and when there is a loss of spontaneous movement they are injected subcutaneously in the dorsal surface of the hindpaw with 50 $\mu$l of 5% formalin solution using a 30 gauge needle. Rats are then individually placed in an open Plexiglas chamber for observation, and within a maximum interval of 1 to 2 min, the animals display recovery from anesthesia with spontaneous activity and normal motor function. Pain behavior is quantified by periodically counting the incidents of spontaneous flinching/shaking of the injected paw. The flinches are counted for 1-min periods at 1- to 2-, 5- to 6- and 5 min intervals during the interval from 10 to 60 min. Inhibition of the pain behavior is demonstrative of an analgesic activity.

All $ED_{50}$ values and their standard errors of the mean (S.E.M.) are determined using accepted numerical methods. For example, see R. E. Kirk (1982) Experimental Design: Procedures for the behavioral sciences, 2nd ed. Belmont, Calif.: Brooks/Cole Publishing Co. The interaction of the dosages on analgesia is demonstrated graphically by the Loewe isobologram (S. Loewe, Pharm. Rev. 9:237–242, 1957).

The interaction of an atypical antipsychotic and another compound used in the treatment of pain on analgesia is demonstrated by Loewe isobologram analysis. In the isobolographic analysis, the analgesic effects of an atypical antipsychotic are presented on the X-axis and of the other compound used in the treatment of pain on the Y-axis. The line connecting the $ED_{50}$ dosages of an atypical antipsychotic alone and another compound used in the treatment of pain alone represents the "ED50 addition line" which indicates the expected location of the $ED_5$ values for an atypical antipsychotic and another compound used in the treatment of pain combinations if simple additivity were to describe their combined effects. According to Loewe's isobolographic theory, if the analgesic effects of an atypical antipsychotic and an another compound used in the treatment of pain were simply additive to one another, the expected location of the $ED_{50}$ values of the an atypical antipsychotic and another compound used in the treatment of pain components of each fixed dosage ratio would lie on the addition line. Combination $ED_{50}$ values located significantly below the $ED_{50}$ addition line would represent unexpectedly enhanced analgesic activity and combination $ED_{50}$ values located above the line would represent unexpected diminished analgesic effect.

One method to establish the significance of such unexpected enhanced or diminished activity is to calculate the SEM values for each $ED_{50}$. If the SEM values do not overlap the line of addition, then the $ED_{50}$ values are significantly different from the line of addition.

Surprisingly, such experiments demonstrate that compositions comprised of an atypical antipsychotic and another compound used in the treatment of pain show a statistically significant synergistic analgesic effect.

It will be apparent that the instant specifications and examples are set forth by way of illustration and not limitation, and that various modifications and changes may be made without departing from the spirit and scope of the present invention.

Such experiments support that atypical antipsychotics and atypical antipsychotic:another Drug Used in the Treatment of Pain compositions can provide an analgesic effect. Such compositions can provide a statistically significant synergistic analgesic effect.

Clinical Observations.

A double-blind multicenter clinical trial is designed to assess the safety and efficacy of the atypical antipsychotic. Patients are randomized to atypical antipsychotic, atypical antipsychotic: another Drug Used in the Treatment of Pain composition of this invention, another Drug Used in the Treatment of Pain alone, or placebo. Patients are monitored for perception of pain using standard methods.

The materials for the present invention can be purchased or prepared by a variety of procedures well known to those of ordinary skill in the art. The atypical antipsychotic compounds are either commercially available or can be prepared using methods described in the patents incorporated herein by reference or as described in widely available publications.

The following examples are provided for purposes of illustration and are not to be construed as limiting the scope of the claimed invention.

EXAMPLE 1

A portion of the hydroxypropyl cellulose was dissolved in purified water to form a solution for granulation. The remaining hydroxypropyl cellulose (total of 4.0% w/w final tablet weight), which was an extra fine grade, was combined with the atypical antipsychtic (1.18% w/w), another Drug Used in the Treatment of Pain (3% w/w), lactose (79.32% w/w) and a portion of the crospovidone (5% w/w) in a high shear granulator. All ingredients were security sieved prior to addition and dry blended in the granulator. This mixture was then granulated with the hydroxypropyl cellulose solution in the high shear granulator. The granulation was wet sized using standard methods. The wet granulation was then dried in a fluidized bed dryer and sized. The material was then added to a tumble bin mixer.

The running powders consisting of microcrystalline cellulose (granular) (10% w/w), magnesium stearate (0.5% w/w), and the remainder of the crospovidone were added to the sized granulation. The mixture was blended and compressed with the appropriate tooling on tablet compression equipment.

Subcoating:

Hydroxypropyl methylcellulose (10% w/w) was mixed with purified water to form a solution. Core tablets were divided into approximately equal sections and spray coated with the hydroxypropyl methylcellulose solution . The operation was performed in a perforated coating pan.

Coating of Core Tablets:

Color Mixture White (hydroxypropyl methylcellulose, polyethylene glycol, polysorbate 80, and titanium dioxide) was mixed with purified water to form the coating suspension. Subcoated tablets were divided into approximately equal sections and spray coated with the coating suspension described above. The operation was performed in a perforated coating pan.

The coated tablets were lightly dusted with carnauba wax and imprinted with appropriate identification.

EXAMPLE 2

A portion of the hydroxypropyl cellulose was dissolved in purified water to form a solution for granulation. The remaining hydroxypropyl cellulose (total of 4.0% w/w final tablet weight), which was an extra fine grade, was combined with the atypical antipsychtic (1.18% w/w), lactose (79.32% w/w) and a portion of the crospovidone (5% w/w) in a high shear granulator. All ingredients were security sieved prior to addition and dry blended in the granulator. This mixture was then granulated with the hydroxypropyl cellulose solution in the high shear granulator. The granulation was wet sized using standard methods. The wet granulation was then dried in a fluidized bed dryer and sized. The material was then added to a tumble bin mixer.

The running powders consisting of microcrystalline cellulose (granular) (10% w/w), magnesium stearate (0.5% w/w), and the remainder of the crospovidone were added to the sized granulation. The mixture was blended and compressed with the appropriate tooling on tablet compression equipment.

Subcoatings:

Hydroxypropyl methylcellulose (10% w/w) was mixed with purified water to form a solution. Core tablets were divided into approximately equal sections and spray coated with the hydroxypropyl methylcellulose solution . The operation was performed in a perforated coating pan.

Coating of Core Tablets:

Color Mixture White (hydroxypropyl methylcellulose, polyethylene glycol, polysorbate 80, and titanium dioxide) was mixed with purified water to form the coating suspension. Subcoated tablets were divided into approximately equal sections and spray coated with the coating suspension described above. The operation was performed in a perforated coating pan.

The coated tablets were lightly dusted with carnauba wax and imprinted with appropriate identification.

We claim:

1. A pharmaceutical composition comprising an atypical antipsychotic which is seroquel or a pharmaceutically acceptable salt or solvate thereof; and one or more Drug Used in the Treatment of Pain in a weight ratio of atypical antipsychotic to another Drug Used in the Treatment of Pain from about one part atypical antipsychotic to from about one (1) to about one thousand (1000) parts Drug Used in the Treatment of Pain.

2. A pharmaceutical composition comprising an atypical antipsychotic which is seroquel or a pharmaceutically acceptable salt or solvate thereof; and one or more Drug Used in the Treatment of Pain in a weight ratio of atypical antipsychotic to another Drug Used in the Treatment of Pain from about one part atypical antipsychotic to from about one (1) to about one hundred (100) parts Drug Used in the Treatment of Pain.

3. A pharmaceutical composition according to claim 2 wherein the Drug Used in the Treatment of Pain is selected from the group consisting of aspirin, ibuprophen, acetaminophen, indomethacin, Tylenol #3, tricyclic antidepressants, anticonvulsants, serotonin reuptake inhibitors, mixed serotonin-norepinephrine reuptake inhibitors, serotonin receptor agonists and antagonists, cholinergic analgesics, adrenergic agents, and neurokinin antagonists.

4. A pharmaceutical composition according to claim 3 wherein the Drug Used in the Treatment of Pain is a serotonin reuptake inhibitor.

5. A pharmaceutical composition according to claim 4 wherein the serotonin reuptake inhibitor is fluoxetine.

6. A pharmaceutical composition according to claim 4 wherein the serotonin reuptake inhibitor is paroxetine.

7. A pharmaceutical composition according to claim 4 wherein the serotonin reuptake inhibitor is sertraline.

8. A pharmaceutical composition according to claim 3 wherein the Drug Used in the Treatment of Pain is a mixed serotonin-norepinephrine reuptake inhibitor.

9. A pharmaceutical composition according to claim 8 wherein the mixed serotonin-norepinephrine reuptake inhibitor is venlafaxine.

10. A pharmaceutical composition according to claim 8 wherein the mixed serotonin-norepinephrine reuptake inhibitor is duloxetine.

* * * * *